United States Patent
Dur et al.

(10) Patent No.: US 11,883,641 B2
(45) Date of Patent: Jan. 30, 2024

(54) AXIAL FLOW BLOOD PUMP

(71) Applicant: TC1 LLC, St. Paul, MN (US)

(72) Inventors: Onur Dur, Milpitas, CA (US); Kevin Bourque, Reading, MA (US)

(73) Assignee: TC1 LLC, St. Paul, MN (US)

( * ) Notice: Subject to any disclaimer, the term of this patent is extended or adjusted under 35 U.S.C. 154(b) by 0 days.

(21) Appl. No.: 17/983,265

(22) Filed: Nov. 8, 2022

(65) Prior Publication Data

US 2023/0066175 A1 Mar. 2, 2023

Related U.S. Application Data

(60) Continuation of application No. 17/008,984, filed on Sep. 1, 2020, now Pat. No. 11,511,104, which is a
(Continued)

(51) Int. Cl.
*A61M 60/419* (2021.01)
*A61M 60/82* (2021.01)
(Continued)

(52) U.S. Cl.
CPC ........ *A61M 60/419* (2021.01); *A61M 60/148* (2021.01); *A61M 60/178* (2021.01); *A61M 60/242* (2021.01); *A61M 60/422* (2021.01); *A61M 60/812* (2021.01); *A61M 60/82* (2021.01); *A61M 60/824* (2021.01);
(Continued)

(58) Field of Classification Search
None
See application file for complete search history.

(56) References Cited

U.S. PATENT DOCUMENTS 4,507,048 A * 3/1985 Belenger ............. A61M 60/825
  415/90
5,507,629 A 4/1996 Jarvik
(Continued)

FOREIGN PATENT DOCUMENTS

WO 9853864 A1 12/1998
WO 2012054435 A1 4/2012
(Continued)

*Primary Examiner* — Ankit D Tejani
(74) *Attorney, Agent, or Firm* — Kilpatrick Townsend & Stockton LLP

(57) ABSTRACT

The invention generally relates to improved medical blood pump devices, systems, and methods. For example, blood pumps may be provided that include a housing defining a blood flow path between an inlet and an outlet. A rotor may be positioned in the blood flow path. A motor stator may be driven to rotate the rotor to provide the blood flow through the pump. Axial and/or tilt stabilization components may be provided to increase an axial and/or tilt stabilization of the rotor within the blood flow path. In some embodiments, biasing forces are provided that urge the rotor toward a bearing component. The biasing force may be provided by adjusting drive signals of the motor stator. Additionally, or alternatively, one or more magnets (e.g., permanent/stator magnets) may be provided to bias the rotor in the upstream and/or downstream direction (e.g., toward a bearing (chamfer, step, conical), or the like).

20 Claims, 5 Drawing Sheets

Related U.S. Application Data division of application No. 15/807,398, filed on Nov. 8, 2017, now Pat. No. 10,780,207, which is a continuation of application No. PCT/US2016/032516, filed on May 13, 2016.

(60) Provisional application No. 62/162,205, filed on May 15, 2015.

(51) Int. Cl.
*A61M 60/148* (2021.01)
*A61M 60/422* (2021.01)
*A61M 60/824* (2021.01)
*A61M 60/812* (2021.01)
*A61M 60/242* (2021.01)
*A61M 60/178* (2021.01)

(52) U.S. Cl.
CPC ............... *A61M 2205/8206* (2013.01); *A61M 2209/088* (2013.01)

(56) References Cited

U.S. PATENT DOCUMENTS

| | | | |
|---|---|---|---|
| 5,695,471 A | 12/1997 | Wampler | |
| 5,888,242 A | 3/1999 | Antaki et al. | |
| 6,071,093 A | 6/2000 | Hart | |
| 6,116,862 A | 9/2000 | Rau et al. | |
| 6,186,665 B1 | 2/2001 | Maher et al. | |
| 6,227,820 B1 | 5/2001 | Jarvik | |
| 6,234,772 B1 | 5/2001 | Wampler et al. | |
| 6,254,359 B1 | 7/2001 | Aber | |
| 6,264,635 B1 | 7/2001 | Wampler et al. | |
| 6,527,699 B1 | 3/2003 | Goldowsky | |
| 6,688,861 B2 | 2/2004 | Wampler | |
| 6,991,595 B2 | 1/2006 | Burke et al. | |
| 7,431,688 B2 | 10/2008 | Wampler et al. | |
| 7,487,641 B2 | 2/2009 | Frechette et al. | |
| 7,699,586 B2 | 4/2010 | LaRose et al. | |
| 7,976,271 B2 | 7/2011 | LaRose et al. | |
| 7,997,854 B2 | 8/2011 | LaRose et al. | |
| 8,007,254 B2 | 8/2011 | LaRose et al. | |
| 8,152,493 B2 | 4/2012 | LaRose et al. | |
| 8,323,174 B2 | 12/2012 | Jeevanandam et al. | |
| 8,419,609 B2 | 4/2013 | Shambaugh, Jr. et al. | |
| 8,449,444 B2 | 5/2013 | Poirier | |
| 8,506,471 B2 | 8/2013 | Bourque | |
| 8,562,508 B2 | 10/2013 | Dague et al. | |
| 8,597,350 B2 | 12/2013 | Rudser et al. | |
| 8,652,024 B1 | 2/2014 | Yanai et al. | |
| 8,657,733 B2 | 2/2014 | Ayre et al. | |
| 8,668,473 B2 | 3/2014 | LaRose et al. | |
| 8,672,611 B2 | 3/2014 | LaRose et al. | |
| 8,721,517 B2 | 5/2014 | Butler et al. | |
| 8,807,968 B2 | 8/2014 | Lancisi et al. | |
| 8,894,387 B2 | 11/2014 | White et al. | |
| 9,717,832 B2 | 8/2017 | Taskin et al. | |
| 2005/0071001 A1 | 3/2005 | Jarvik | |
| 2005/0135942 A1* | 6/2005 | Wood | F16C 32/044 417/423.12 |
| 2007/0078293 A1 | 4/2007 | Shambaugh et al. | |
| 2007/0231135 A1 | 10/2007 | Wampler et al. | |
| 2008/0021394 A1 | 1/2008 | LaRose et al. | |
| 2009/0180887 A1 | 7/2009 | Mischo et al. | |
| 2009/0203957 A1 | 8/2009 | LaRose et al. | |
| 2011/0238172 A1 | 9/2011 | Akdis et al. | |
| 2011/0275884 A1 | 11/2011 | Scheckel et al. | |
| 2011/0301403 A1* | 12/2011 | LaRose | F04D 29/0476 416/235 |
| 2012/0046514 A1 | 2/2012 | Bourque | |
| 2012/0095281 A1 | 4/2012 | Reichenbach et al. | |
| 2012/0245680 A1* | 9/2012 | Masuzawa | A61M 60/538 623/3.11 |
| 2013/0096364 A1 | 4/2013 | Reichenbach et al. | |
| 2013/0121804 A1 | 5/2013 | Oliphant et al. | |
| 2013/0121821 A1 | 5/2013 | Ozaki et al. | |
| 2013/0127253 A1 | 5/2013 | Stark et al. | |
| 2013/0170970 A1 | 7/2013 | Ozaki et al. | |
| 2013/0177409 A1 | 7/2013 | Schumacher et al. | |
| 2013/0183176 A1 | 7/2013 | Wampler et al. | |
| 2013/0225909 A1 | 8/2013 | Dormanen et al. | |
| 2013/0314047 A1 | 11/2013 | Eagle et al. | |
| 2013/0330219 A1 | 12/2013 | LaRose et al. | |
| 2013/0338559 A1 | 12/2013 | Franano et al. | |
| 2014/0314597 A1* | 10/2014 | Allaire | A61M 60/178 417/420 |
| 2014/0322011 A1 | 10/2014 | Wampler et al. | |
| 2015/0118021 A1 | 4/2015 | Larose et al. | |
| 2018/0064861 A1 | 3/2018 | Dur et al. | |

FOREIGN PATENT DOCUMENTS

| | | |
|---|---|---|
| WO | 2012054490 A1 | 4/2012 |
| WO | 2015189590 A1 | 12/2015 |
| WO | 2016130944 | 8/2016 |

* cited by examiner

AXIAL FLOW BLOOD PUMP

CROSS REFERENCE TO RELATED APPLICATIONS

The present application is a Continuation of U.S. patent application Ser. No. 17/008,984 filed Sep. 1, 2020 (Allowed); which is a Divisional of U.S. patent application Ser. No. 15/807,398 filed Nov. 8, 2017 (now U.S. Pat. No. 10,780,207); which is a Continuation of PCT/US2016/032516 filed May 13, 2016; which claims the benefit of U.S. Provisional Appln No. 62/162,205 filed May 15, 2015; the disclosures which are incorporated herein by reference in their entirety for all purposes.

BACKGROUND

This application relates generally to mechanical circulatory support systems, and more specifically relates to stabilization components for an implantable blood pump.

Ventricular assist devices, known as VADs, are implantable blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

While blood pumps have been effective for patients, further improvements may be desirable. For example, increased impeller stabilization in an axial and/or tilt direction may be beneficial. In particular, increased tilt and/or axial stabilization of an axial flow blood pump may be beneficial as such pumps may be more susceptible to tilting and/or wobbling within the blood flow path.

BRIEF SUMMARY

In some aspects, an axial flow mechanical circulatory support system may be provided. The support system may include a housing having an inlet, an outlet, and an internal wall defining a flow path from the inlet to the outlet. An impeller may be positioned within the housing flow path. The impeller may include a magnetic member and may include blades for pumping blood in a direction from the inlet to the outlet when the impeller rotates about an axis of rotation. A stator may be positioned about the impeller for generating a magnetic field to rotate the impeller. A bearing may be provided for stabilizing the impeller in an axial direction. The bearing may include a bearing member for applying a bearing force against the impeller in an axial direction from the inlet towards the outlet. The bearing may also include a biasing mechanism for applying a biasing force against the impeller in an axial direction opposite the bearing member while the impeller is at rest.

Optionally, the biasing force may be greater than the bearing force when the impeller is at rest such that the impeller rests against the bearing member when at rest. The biasing member may apply a passive biasing force. The bearing member may apply a passive bearing force. In some embodiments, the biasing force may only be applied when the impeller is rotating.

The stator may form a passive magnetic bearing. For example, a drive signal to the stator may be modified to apply the biasing force on the impeller. The bearing member may be a chamfer bearing. The bearing member may be a step bearing. The bearing member may be one or more magnets around the impeller upstream of an axial center of the impeller. Optionally, the bearing member magnets may include yokes. The biasing mechanism may apply a substantially constant axial force. The impeller may have a magnetic body. Optionally, the stator has windings. In many embodiments, the inlet and the outlet are axially aligned.

In further aspects, a blood pump may be provided that includes a housing with an inner wall defining an inlet, an outlet downstream from the inlet, and a blood flow path between the inlet and the outlet. A first portion of the inner wall may have a first inner dimension that increases to a second inner dimension in a downstream direction. An impeller may be included with a magnetic material. The impeller may be positioned within the blood flow path downstream of the first portion of the inner wall. The impeller may have an outer dimension that is greater than the first inner dimension of the inner wall such that the first portion of the inner wall may prevent the impeller from advancing upstream of the first portion of the inner wall. A motor stator may be positioned about the blood flow path between the inlet and the outlet. The motor stator, during operation, may be configured to generate a magnetic field for suspending the impeller within the blood flow path. The magnetic field generated by the motor stator may bias the impeller to urge the impeller in an upstream direction toward the first portion of the inner wall so as to stabilize the impeller in an axial direction.

The magnetic field of the motor stator may urge the impeller in the upstream direction and axial hydrodynamic forces between the impeller and the first portion of the inner wall may be configured to provide increased stabilization of the impeller in an axial direction. The blood pump may avoid the use of permanent magnets in some embodiments. In other embodiments, a first permanent magnet may be provided for producing a first permanent magnetic field urging the impeller in the downstream direction and a second permanent magnet may be provided for producing a second permanent magnetic field urging the impeller in the upstream direction. The magnetic fields of the first permanent magnet and the second permanent magnet may be configured to provide increased stabilization of the impeller in the axial direction. The first permanent magnet and the second permanent magnet may be ring magnets positioned about the blood flow path.

A first conical bearing may extend from the inner wall of the housing and into the blood flow path. The impeller may cooperate with the first conical bearing to provide increased stabilization of the impeller in a tilt direction. The magnetic fields of the first permanent magnet and the second permanent magnet may be configured to cumulatively urge the impeller towards the first conical bearing. A yoke may be disposed about the motor stator. The yoke may be configured to increase a magnetic flux density associated with the motor stator. A yoke may be disposed about the first permanent magnet. The yoke may be configured to increase a magnetic flux density associated with the first permanent magnet. A yoke may be disposed about the second permanent magnet. The yoke may be configured to increase a magnetic flux density associated with the second permanent magnet. The magnetic fields of the first permanent magnet and the second permanent magnet may be configured to cumulatively urge the impeller in an upstream direction towards the first portion of the inner wall.

A first conical bearing may extend from the inner wall of the housing and into the blood flow path. The impeller may cooperate with the first conical bearing to provide increased stabilization of the impeller in a tilt direction. The impeller may have a hub with a conical upstream portion configured to cooperate with the first conical bearing to provide increased stabilization of the impeller in the tilt direction. The impeller may have a hub with a conical downstream portion configured to cooperate with the first conical bearing to provide increased stabilization of the impeller in the tilt direction. The impeller may have blades extending radially from a hub. The blades may have a beveled downstream edge configured to cooperate with the first conical bearing to provide increased stabilization of the impeller in the tilt direction.

In further aspects, a method of operating an blood pump may be provided. The pump may have a housing with an inner wall defining an inlet, an outlet downstream from the inlet, and a blood flow path between the inlet and the outlet. A first portion of the inner wall may have a first inner dimension that increases to a second inner dimension in a downstream direction. The pump may further include an impeller having a magnetic material and positioned within the blood flow path downstream of the first portion of the inner wall. The impeller may have an outer dimension that is greater than the first inner dimension of the inner wall such that the first portion of the inner wall prevents the impeller from advancing upstream of the first portion of the inner wall. The method may include operating a motor stator positioned about the blood flow path between the inlet and the outlet to generate a magnetic field for suspending the impeller within the blood flow path. Operating the motor stator to produce a magnetic field configured to bias the impeller such that the impeller is urged in an upstream direction toward the first portion of the inner wall so as to stabilize the impeller in an axial direction.

A blood pump may be provided with a housing with an inner wall defining an inlet, an outlet downstream from the inlet, and a blood flow path between the inlet and the outlet. An impeller may include a magnetic material and may be positioned within the blood flow path. A motor stator may be positioned about the blood flow path between the inlet and the outlet. The motor stator, during operation, may be configured to suspend the impeller within the blood flow path. A first permanent magnet may produce a first permanent magnetic field urging the impeller in the downstream direction. A second permanent magnet may produce a second permanent magnetic field urging the impeller in the upstream direction. The magnetic fields of the first permanent magnet and the second permanent magnet may be configured to provide increased stabilization of the impeller in an axial direction.

The first permanent magnet and the second permanent magnet may be ring magnets positioned about the blood flow path. A first conical bearing may extend from the inner wall of the housing and into the blood flow path. The impeller may cooperate with the first conical bearing to provide increased stabilization of the impeller in a tilt direction. The impeller may have a hub with a conical upstream portion configured to cooperate with the first conical bearing to provide increased stabilization of the impeller in the tilt direction. The first conical bearing may comprise a surface angled at 45 degrees relative to an axis of rotation of the impeller to provide tilt and axial hydrodynamic forces. The surface of the conical upstream portion of the hub may angle toward the axis of rotation of the impeller at 45 degrees. The radial and axial hydrodynamic forces between the surface of the first conical bearing and the surface of the conical upstream portion of the hub may increase stabilization of the impeller in the tilt and axial direction. The impeller may have a hub with a conical downstream portion configured to cooperate with the first conical bearing to provide increased stabilization of the impeller in the tilt direction. The first conical bearing may have a surface angled at 45 degrees relative to an axis of rotation of the impeller to provide radial and axial hydrodynamic forces. A surface of the conical downstream portion of the hub may angle toward the axis of rotation of the impeller at degrees. The radial and axial hydrodynamic forces between the surface of the first conical bearing and the surface of the conical downstream portion of the hub may increase stabilization of the impeller in the tilt and axial direction.

The impeller may include blades extending radially from a hub. The blades may have beveled upstream edges configured to cooperate with the first conical bearing to provide increased stabilization of the impeller in the tilt direction. The first conical bearing may have a surface angled at 45 degrees relative to an axis of rotation of the impeller to provide radial and axial hydrodynamic forces. The blade tips of beveled upstream edges of the blades of the impeller may angle toward the axis of rotation of the impeller at 45 degrees. The radial and axial hydrodynamic forces between the surface of the first conical bearing and blade tips of beveled upstream edges of the blades of the impeller may increase stabilization of the impeller in the tilt and axial direction.

A second conical bearing may extend from the inner wall of the housing and into the blood flow path. The second conical bearing may be positioned downstream from the first conical bearing. An upstream portion of the impeller may cooperate with the first conical bearing and a downstream portion of the impeller may cooperate with the second conical bearing to provide increased stabilization of the impeller in the tilt direction.

Optionally the magnetic fields of the first permanent magnet and the second permanent magnet cumulatively urge the impeller towards the first conical bearing. A yoke may be disposed about the motor stator. The yoke may be configured to increase a magnetic flux density of the motor stator. A yoke may be disposed about the first permanent magnet. The yoke may be configured to increase a magnetic flux density of the first permanent magnet. A yoke may be disposed about the second permanent magnet. The yoke may be configured to increase a magnetic flux density of the second permanent magnet.

A first portion of the inner wall may have a first inner dimension that increases to a second inner dimension in a downstream direction. The impeller may have an outer dimension that is greater than the first inner dimension of the inner wall such that the first portion of the inner wall prevents the impeller from advancing upstream of the first portion of the inner wall. The magnetic fields of the first permanent magnet and the second permanent magnet may cumulatively urge the impeller in an upstream direction towards the first portion of the inner wall. A magnetic field generated by the motor stator may be configured to bias the impeller such that the magnetic field of the motor stator urges the impeller in an upstream direction toward the first portion of the inner wall.

In further aspects a blood pump may be provided. A housing with an inner wall may define an inlet, an outlet downstream from the inlet, and a blood flow path between the inlet and the outlet. An impeller may include a magnetic material and may be positioned within the blood flow path. A motor stator may be positioned about the blood flow path between the inlet and the outlet. The motor stator, during operation, may be configured to generate a magnetic field for suspending the impeller within the blood flow path. A first conical bearing may extend from the inner wall of the housing and into the blood flow path. The impeller may cooperate with the first conical bearing to provide increased stabilization of the impeller in a tilt direction. The magnetic field generated by the motor stator may be configured to bias the impeller such that the magnetic field urges the impeller toward the first conical bearing so as to stabilize the impeller in an axial direction. The magnetic field of the motor stator urging the impeller toward the first conical bearing and axial hydrodynamic forces between the impeller and the first conical bearing may be configured to provide increased stabilization of the impeller in an axial direction. The impeller may have a hub with a conical upstream portion configured to cooperate with the first conical bearing to provide increased stabilization of the impeller in the tilt direction. The impeller may have a hub with a conical downstream portion configured to cooperate with the first conical bearing to provide increased stabilization of the impeller in the tilt direction.

The impeller may include blades extending radially from a hub. The blades may have beveled downstream edges configured to cooperate with the first conical bearing to provide increased stabilization of the impeller in the tilt direction.

The blood pump may further include a first permanent magnet producing a first permanent magnetic field urging the impeller in the downstream direction. A second permanent magnet may be producing a second permanent magnetic field urging the impeller in the upstream direction. The magnetic fields of the first permanent magnet and the second permanent magnet may be configured to provide increased stabilization of the impeller in the axial direction. A yoke may be disposed about the motor stator. The yoke may be configured to increase a magnetic flux density of the motor stator. A yoke may be disposed about the first permanent magnet. The yoke may be configured to increase a magnetic flux density of the first permanent magnet. A yoke may be disposed about the second permanent magnet. The yoke may be configured to increase a magnetic flux density of the second permanent magnet.

A second conical bearing may extend from the inner wall of the housing and into the blood flow path. The second conical bearing may be positioned downstream from the first conical bearing. An upstream portion of the impeller may cooperate with the first conical bearing and a downstream portion of the impeller may cooperate with the second conical bearing to provide increased stabilization of the impeller in the tilt direction.

In even further aspects, a blood pump may be provided with a housing with an inner wall defining an inlet, an outlet downstream from the inlet, and a blood flow path between the inlet and the outlet. A first portion of the inner wall may have a first inner dimension that increases to a second inner dimension in an upstream direction. An impeller may include a magnetic material and may be positioned within the blood flow path upstream of the first portion of the inner wall. The impeller may have an outer dimension that is greater than the first inner dimension of the inner wall such that the first portion of the inner wall prevents the impeller from advancing downstream of the first portion of the inner wall. A motor stator may be positioned about the blood flow path between the inlet and the outlet. The motor stator, during operation, may be configured to generate a magnetic field for suspending the impeller within the blood flow path. The magnetic field generated by the motor stator may be configured to apply a biasing force on the impeller such that the magnetic field urges the impeller in a downstream direction toward the first portion of the inner wall. The magnetic field of the motor stator may urge the impeller in the downstream direction and axial hydrodynamic forces between the impeller and the first portion of the inner wall may be configured to provide increased stabilization of the impeller in an axial direction.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor it is intended to be used in isolation to determine the scope of the claimed subject matter. The subject matter should be understood by reference to appropriate portions of the entire specification of this patent, any or all drawings and each claim. The invention will be better understood upon reading the following description and examining the figures which accompany it.

BRIEF DESCRIPTION OF THE DRAWINGS

Further details, aspects, and embodiments of the invention will be described by way of example only and with reference to the drawings. In the drawings, like reference numbers are used to identify like or functionally similar elements. Elements in the figures are illustrated for simplicity and clarity and have not necessarily been drawn to scale.

DETAILED DESCRIPTION

Figure 1:
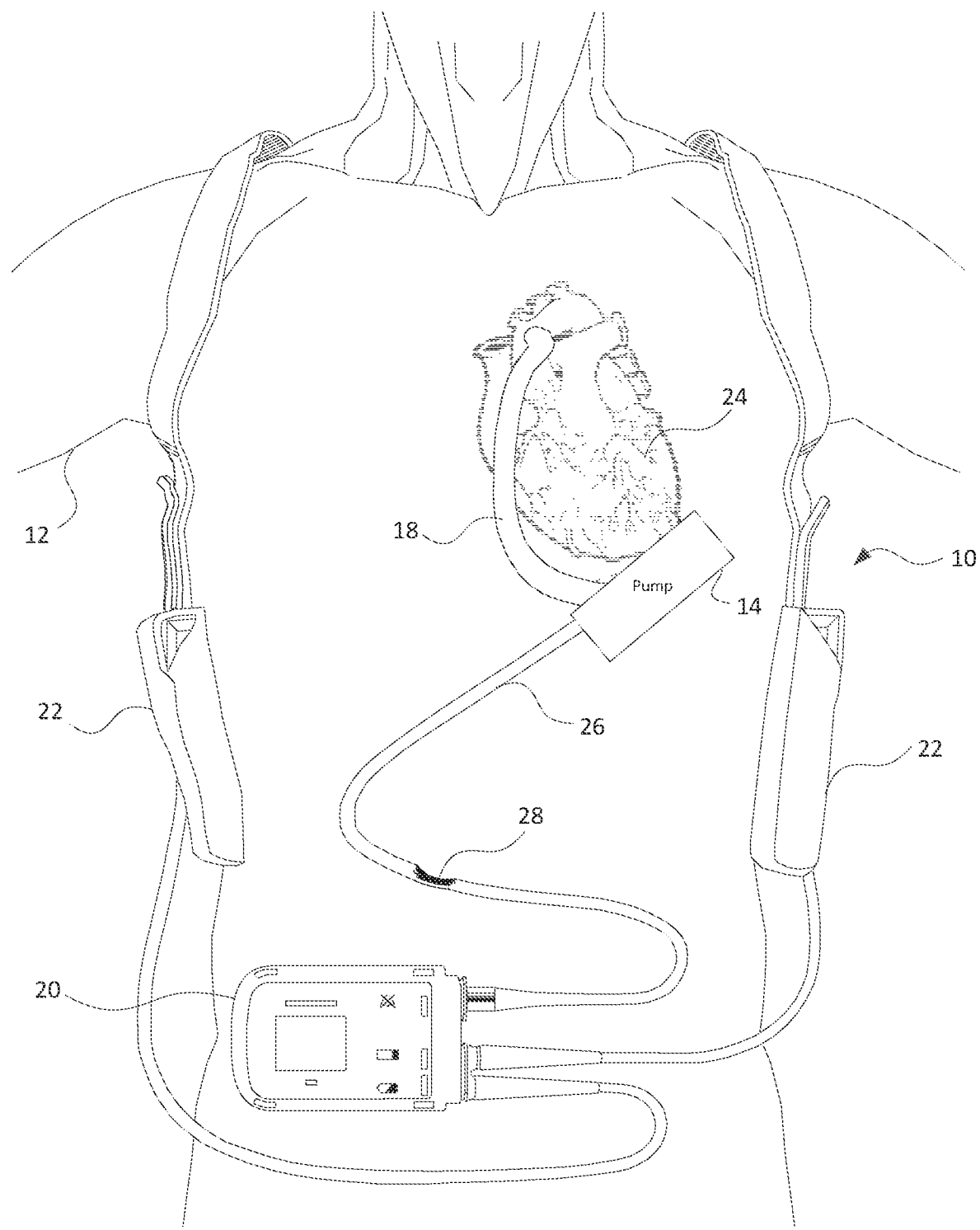
FIG. 1 is an illustration of a mechanical circulatory support system implanted in a patient's body.
Figure 2:
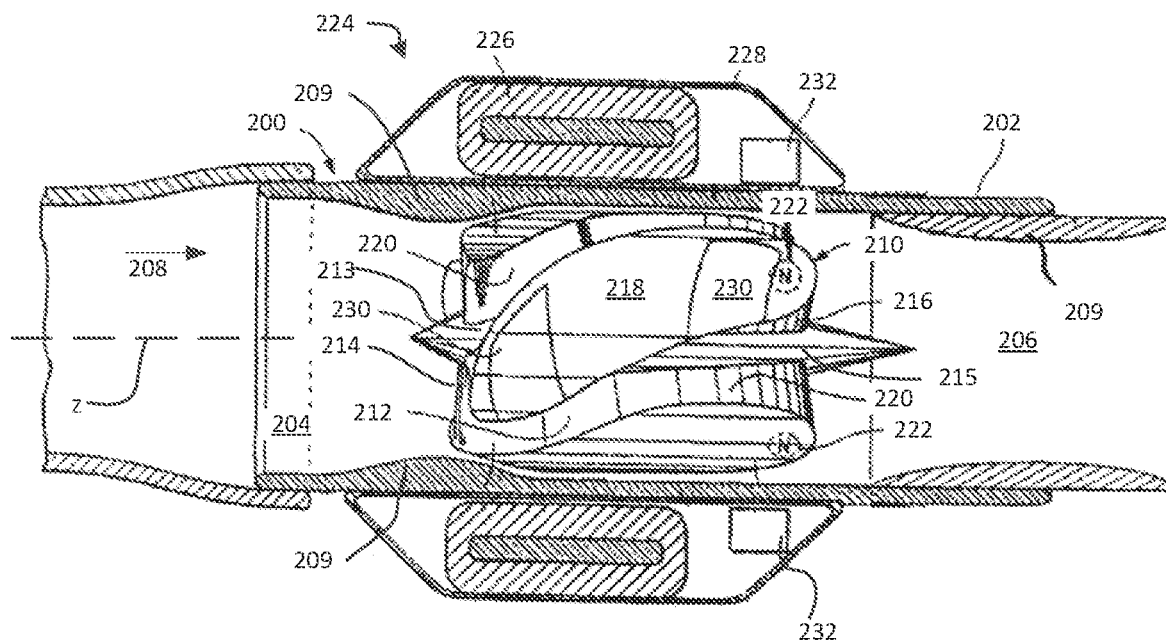
FIG. 2 illustrates a blood pump with stabilization components according to some embodiments of the present invention.

FIG. 1 is an illustration of a mechanical circulatory support system 10 implanted in a patient's body 12. The mechanical circulatory support system 10 comprises an implantable blood pump 14, outflow cannula 18, system controller 20, and power sources 22. The implantable blood pump 14 may comprise a VAD that is attached to an apex of the left ventricle, as illustrated, or the right ventricle, or both ventricles of the heart 24. The VAD may comprise a centrifugal or axial flow pump as described in further detail herein that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,419,609, 8,852,072, 8,652,024, 8,668,473, 8,864,643, 8,882,744, 9,068,572, 9,091,271, 9,265,870, 9,382,908, all of which are incorporated herein by reference for all purposes in their entirety. With reference to FIGS. 1 and 2, the blood pump 14 may be attached to the heart 24 via a ventricular cuff which is sewn to the heart 24 and coupled to the blood pump 14. The other end of the blood pump 14 connects to the ascending aorta via the outflow cannula 18 so that the VAD effectively diverts blood from the weakened ventricle and propels it to the aorta for circulation to the rest of the patient's vascular system.

FIG. 1 illustrates the mechanical circulatory support system 10 during battery 22 powered operation. A driveline 26 which exits through the patient's abdomen 28, connects the implanted blood pump 14 to the system controller 20, which monitors system 10 operation. Related controller systems applicable to the present invention are described in greater detail below and in U.S. Pat. Nos. 5,888,242, 6,991,595, 8,323,174, 8,449,444, 8,506,471, 8,597,350, and 8,657,733 and U.S. Patent Publication Nos. 2005/0071001 and 2013/0314047, all of which are incorporated herein by reference for all purposes in their entirety. The system may be powered by either one, two, or more batteries 22. It will be appreciated that although the system controller 20 and power source 22 are illustrated outside/external to the patient body, the driveline 26, system controller 20 and/or power source 22 may be partially or fully implantable within the patient, as separate components or integrated with the blood bump 14. Examples of such modifications are further described in U.S. Pat. Nos. 8,562,508 and 9,079,043, all of which are incorporated herein by reference for all purposes in their entirety.

Pump 14 may include an impeller suspended in a blood flow path. As the impeller rotates within the blood flow path about its axis, the impeller may experience forces that can destabilize the impeller within the blood flow path. These forces may cause: 1) axial destabilization where the impeller translates in the axial direction from a desired position (e.g., in an upstream or downstream direction), 2) radial destabilization where the axis of the impeller translates from a desired position in a direction perpendicular to the axial direction (e.g., off-center with the blood flow path or the like), and/or 3) tilt destabilization where the impeller rotates about a direction perpendicular to the axial direction (e.g., impeller "wobbling").

FIG. 2 illustrates an exemplary pump 200 according to some embodiments. Blood pump 200 may be configured to assist in pumping blood through a patient's vascular system. The pump 200 may include a housing 202. The housing 202 may be non-magnetic and may be made of suitable biocompatible material such as titanium or a suitable ceramic material which is non-thrombogenic, rigid, and exhibits minimum eddy current losses. The housing 202 may define a blood inlet 204, a blood outlet 206, and a blood flow path between the inlet 204 and the outlet 206 so that blood flows through the housing 202 in the direction shown by the arrow 208. In some embodiments, housing 202 may have a constant exterior diameter while the inlet portion of its interior diameter may first converge and thereafter diverge so as to define a constriction 209 in the blood flow path.

A rotor 210 may be positioned within the blood flow path defined by the housing 202, and may act as an impeller for pumping fluid along the blood flow path. Rotor 210 may have one or more grooves 212 each of which extends from an entry section or inlet channel 213 at the leading edge 214 to an exit section or outlet channel 215 at the trailing edge 216 of the rotor 210. The grooves 212 define fluid flow channels across the rotor 210. In some embodiments a plurality of grooves 212 formed in the rotor 210 are spaced apart and define a plurality of blades with blade tips 218 therebetween. Each groove 212 is defined by a pair of side walls 220 extending substantially radially to the rotational axis of the rotor 210, but not necessarily parallel to each other.

Each of the grooves 212 may have a central flow channel that curves at least partially around the rotational axis of the rotor 210 and opens into a substantially axially extending outlet channel 215. The curved central portion may be narrower than the inlet channel 213 or outlet channel 215. The relatively wide outlet channel 215 and its axial orientation may enhance the discharge flow characteristics of the blood being pumped by more easily allowing for the release of blood from the rotor 210. The grooves 212 and their side walls 220 may drive blood in the axial direction, shown by the arrow 208, as the rotor 210 is rotated (clockwise in the embodiment of FIG. 2).

In one embodiment, the number of grooves 212 may be in the range of from 2 to 8, with four being typical. Irrespective of the number of grooves 212, their collective widths at the periphery of the rotor 210 may be equal to or substantially less than the collective, total circumferential width at of the blade tips 218 between the grooves 212. Collectively, the total width of the grooves 212 may be less than or equal to the collective, total width of the respective widths of the blade tip 218.

In this embodiment, the depth of each of the grooves 212 is greater than the radial extent of the blades in comparable and conventional thin blade axial pump designs. For example, for heart pump 200 uses the height of the rotor blades from the axis of rotation of the rotor 210 to their outer tips 218 may be at least 2 mm, up to typically about 10 mm. Alternatively, the average depth of the grooves 212 from their outer perimeters may fall within the range of from 1 mm to 5 mm. In some embodiments the average depth of the grooves 212 is approximately ⅓ the diameter of the rotor 210, but is less than the radius of the rotor 210. In other embodiments the grooves 212 may be deeper at the entry channel 213 at the leading edge 214 of the rotor 210 and shallower at the exit channel 215 at the trailing edge 216 of the rotor 210.

The blade tips 218 of the rotor 210 are each provided with one or more hydrodynamic thrust bearing surfaces 230. Each of the thrust bearing surfaces 230 is disposed along the surface of the associated blade tip having a prescribed peripheral radius. The leading edge of each of the bearing surfaces 230 from the viewpoint of the (clockwise) spin of the rotor 210, is recessed by a predetermined amount below the surface of the associated blade tip 218. The recessed surface then tapers in a gradual, curved manner across the blade tip 218 along an arc, the axis of curvature of which is not necessarily co-axial with the rotational axis of the rotor 210. The tapered bearing surface 230 terminates at a rear end, at which point each bearing surface 230 is feathered into the periphery of the blade tip 218 with a smooth transition and is no longer recessed with respect to the continuing downstream surface of the land area.

As the rotor 210 rotates, the respective thrust bearings 230 on each blade tip 281 scoop blood onto the bearing surfaces 230 whereby it flows between the bearing surfaces and the inner wall of the tubular pump housing 202. The effect of the tapered configuration of the thrust bearing surfaces 230 is to force blood to flow through a decreasing or constricting area created between the bearing surfaces 230 and the inner wall of the tubular pump housing 202.

This results in increasing fluid pressure upstream within the constriction, which pressure acts against the bearing surface areas 230 and produces a net symmetrical force for radial support of the spinning rotor 210. The hydrodynamic force that is thus created on the surfaces of the rotor blade tips 218 tends to hold the rotor 210 suspended and centered within the lumen of the tubular housing 20 in a manner shown in FIG. 2, and resists dynamic, radial shock loading forces without the need for physically contacting bearing surfaces. The thrust bearing surfaces 230 may be formed directly into the peripheral surfaces of the blade tips 218 or may be placed within suitable cavities formed in the outer peripheral surfaces of the blade tips 218 and held in place by a suitable cover.

In some embodiments, hydrodynamic thrust bearing surfaces 230 are created on the leading 214 or trailing edge portions 216 of the rotor 210. For example, with reference to FIG. 2, the bearing 230 at the leading edge 214 of the rotor 210 is tapered or beveled toward the axis of the rotor 210 to cooperate with the constriction 209 of the tubular pump housing 202. Such a thrust bearing 230 would resist longitudinal movement of the rotor to the left, as shown in FIG. 2 as an outer dimension of the rotor 210 is greater than the dimension of the constriction 209. Alternatively, the constriction 209 may, if desired, comprise hydrodynamic thrust bearings cooperating with the adjacent rotor surface to prevent contact between the rotor 210 and the constriction 209 as the rotor 210 rotates.

Hydrodynamic thrust bearing surfaces may also be located on the rotor 210 near its trailing edge 216, in which event the inner diameter of the tubular pump housing 202 near its outlet end 206 would be constricted as shown in FIG. 2 to define a constriction 209. Such thrust bearings on the rotor 210 or formed on a side of the constriction would serve the similar purpose of replacing or of supplementing the attractive magnetic poles of magnets 56 and 57 described below. Such thrust bearings may provide one or both of radial and axial support for the rotor 210 and serve to increase the resistance to shock loading thereby improving rotor 210 stability.

Hydrodynamic thrust bearings 230 on the outer periphery of the rotor 210 provide good surface washing. Centrifugal forces created by thrust bearings 230 tend to push fluid toward the periphery of the housing 202 interior, providing increased blood flow, which can improve the pump's resistance to thrombosis. Thus, since by this invention, conditions are provided that reduce blood coagulation, a lower amount of anticoagulant may be used with the blood pump 200 and patient, which may result in fewer patient adverse side effects. If desired, hydrodynamic thrust bearing surfaces 230 may be aligned in a helical fashion on the surfaces of the rotor 210 to improve surface washing by the moving blood as the rotor spins.

As an alternative to hydrodynamic thrust bearings 230 acting axially on the rotor 210, or in addition thereto, permanent rotor retaining magnets 222 may be placed in each blade tip 218 within the lead 214, trailing 216 or both ends of the rotor 210. One or more corresponding permanent magnets 232 may be placed within or on the tubular pump housing 202 adjacent each rotor retaining magnet 222 to effect attractive magnetic forces acting to retain the axial alignment of the rotor 210 within the housing 202. By way of example only, a permanent magnet 222 is shown in FIG. 2 on a blade tip 218 at the trailing end 216 of the rotor 210. A corresponding permanent stator magnet 232 is placed within the enclosure 228 surrounding the tubular housing 202. The rotor magnet 222 may be formed by magnetizing suitable rotor material. If the north pole of the rotor magnet 222 and the south pole of the stator magnet 232 are adjacent or face each other, as shown in FIG. 2, the attracting magnetic forces will assist in retaining the rotor 210 in the proper axial position. Longitudinal or axial movement of the rotor 210 to the right is thereby restricted by the attractive action of magnets 222 and 232. Of course, magnetic south poles of magnet 222 could be directed to face a north pole of magnet 232 in similar manner, to achieve a generally similar effect. It will be understood that the magnet 232 may comprise a ring magnet or an electromagnetic coil.

In some embodiments the stator magnet 232 may be placed upstream of the corresponding magnets 222. As such the magnet 232 may urge the rotor 210 upstream toward the upstream constriction 209. While illustrated at the trailing end 216 of rotor 210, it should be understood that magnets 222 may be placed at a leading end 214 and magnets 232 may be positioned axially upstream from the magnets 222 at the leading end 214 so as to provide an attracting force on the rotor 210 toward the constriction 209. Additionally in some embodiments, the magnets 232 may be positioned within the constriction 209 portion of housing 202 to provide the attracting force between the upstream constriction portion 209 and the rotor 210.

In further embodiments, the magnet 232 may be placed axially downstream from magnets 222 of rotor 210. An attraction force between the magnets 232 and 222 may be configured to urge the rotor 210 toward a downstream constriction 209 to provide the axial stabilization. In some embodiments, the magnet 232 may be positioned within the downstream constriction 209 to provide the attractive axially stabilizing force between the rotor 210 and the housing 202. Thus, in some embodiments, pump 200 may not include an upstream constriction 209 and may rely on a downstream constriction. In some embodiments, rather than using attracting ends of the magnets 232 and 222, repulsing ends of the magnets 232 and 222 may be used to urge the rotor 210 in a downstream direction toward a downstream constriction 209 so as to provide the increased axial stabilization. In further embodiments, the trailing end 216 of the rotor 210 may experience a force opposite that experienced at the leading end 214 of the rotor 210. For example, the trailing end 216 may experience an attractive force with a corresponding stator magnet 232, while the leading end 214 may experience a repulsive force with a corresponding stator magnet 232, or vice versa. The cumulative magnetic force on the rotor 210 may be configured to urge the rotor 210 toward the upstream constriction 209 or towards a downstream constriction 209. In some embodiments, the pump housing may not have any constrictions and may rely on magnetic forces alone, as will be described further below.

In some embodiments, the rotor 210 may be produced by either machining, molding, or casting a single piece of ferromagnetic material, such as compression bonded neodymium or Alnico (aluminum-nickel alloy), or an alloy of about 70-80 percent by weight of platinum and about 20-30 percent by weight of cobalt. In some embodiments, from essentially 76-79 percent by weight of platinum is present in the alloy. In some embodiments, the alloy may contain essentially from 21-24 percent by weight of cobalt. In one embodiment, an integral, one-piece rotor consists of essentially 77.6 percent by weight of platinum and 22.4 percent by weight of cobalt. Such a rotor is conventionally heat treated to achieve good magnetic properties, and may be magnetized, with North and South magnetic poles, as desired.

The rotor 210 may include a plurality of relatively large permanent drive magnets formed within each of the blade tips 218 of the rotor 210. According to some embodiments of the present invention, the permanent drive magnets in the rotor 210 may be produced by magnetizing selected portions of the peripheries of the blade tips 218. This may be accomplished, for example, by constructing the rotor 210 from a magnetic alloy, which may be isotropic, and magnetizing desired peripheral sections to form a plurality of magnetic poles with various geometric orientations. It is preferable to use a magnetic alloy that is biocompatible so that no additional coating is required. Such a rotor 210 may be easier and less expensive to manufacture than impellers formed from multiple parts.

With reference to FIG. 2, the pump 200 also comprises a motor stator 224 having electrically conductive coils 226. The coils 226 are placed within an enclosure 228 which surrounds the tubular housing 202 and the rotor 210. The motor stator 224 serves to rotate rotor 210 by the conventional application of electric power to the coils 226 to create magnetic flux. The permanent drive magnets incorporated into the blade tips 218 of the rotor 210 are selected for magnetic properties, length, and cross-sectional area in order to provide good electromagnetic coupling with the magnetic flux created by the motor stator 224. Because of the relatively large surface area of the blade tips 218, the nature and placement of the rotor magnets becomes relatively easy to effect. This arrangement provides strong electromagnetic coupling and the necessary magnetic axial stiffness to maintain the rotor in position. In one embodiment, the magnetic coupling between the stator flux and the drive magnets in the rotor 210 creates torque, causing the rotor 210 to rotate clockwise. It will be understood by those skilled in the art that the rotor 210 could be caused to rotate in a counterclockwise direction without departing from the scope of the invention.

The motor 224 may be a three phase, brushless DC motor. In one embodiment the motor 224 could be a toroidal, three phase and wye connected design. The stator 224 may have a back iron design which is consistent with a typical radial flux gap motor. If desired, the motor stator 224 can comprise a separate, hermetically sealed enclosure 228 that slides over the tubular housing 202 into position. A braised weld ring to the enclosure 228 outer surface may be used to secure the motor stator housing 228 in position. Laser welding is one possibility for securing the motor stator enclosure 228 to the housing 202 and obtaining a hermetic seal.

In some embodiments, a drive signal of the motor stator 226 may be configured to bias the rotor 210 toward the constriction 209. In some embodiments, an axial center of the motor stator 226 may be offset from an axial center of the rotor 210. In some embodiments, the axial center of the motor stator 226 may be upstream relative to the axial center of the rotor 210. The offset between the axial centers of the motor stator 226 and the rotor 210 may be configured to urge or bias the rotor 210 toward the constriction 209 thereby providing increased axial stabilization.

Figure 3:
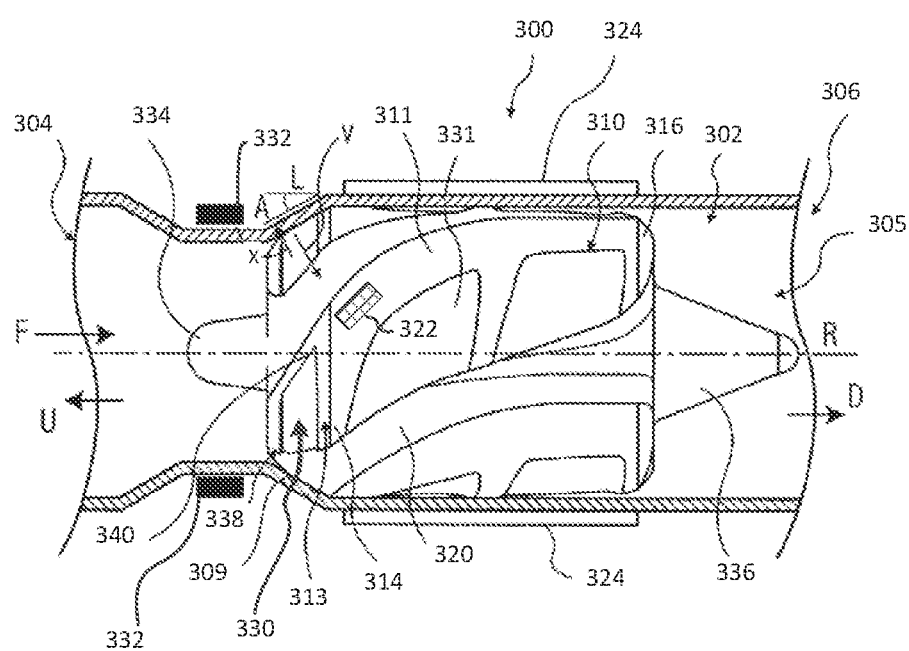
FIG. 3 illustrates another blood pump with stabilization components according to some embodiments of the present invention.

As discussed above, a magnet (e.g., ring magnet or the like) may be positioned about the blood flow path at a position upstream from the rotor to provide an attraction force that urges or biases the rotor toward a constriction. FIG. 3 illustrates an exemplary pump 300 where the ring magnet is positioned within the constriction. Pump 300 includes a rotor 310. The rotor 310 is magnetic and biocompatible, and further includes an upstream end 314, a downstream end 316 and an axis R extending between the ends. The body 310 further includes a plurality of vanes or blades 311 defining a plurality of channels 320 therebetween. The rotor body 310 is constructed and arranged to impel blood downstream, in the direction of fluid flow F, upon rotation of the rotor about axis R in a forward circumferential direction.

Each vane 311 includes at least one hydrodynamic thrust bearing surface 330. As further explained below, each thrust bearing surface 330 is constructed and arranged to apply a hydrodynamic force V (FIG. 3) to the rotor 310 with a component of the force in the downstream direction D upon rotation of the rotor 310 in the clockwise direction (when viewed in the downstream direction). Each vane 311 also has additional radial bearing surfaces 331 along the length of body 310. The radial bearing surfaces are arranged to apply hydrodynamic forces directed generally radially inwardly, toward axis R, upon rotation of the rotor 310.

Each thrust bearing surface 330 has a normal vector X. As referred to herein, the normal vector of a surface is the vector directed out of the surface and perpendicular to the surface. Where the surface is non-planar, the normal vector of the surface as referred to herein should be understood as the integral of the normal vector over the entire extent of the surface. In the embodiment of FIG. 3, the normal vector X of each thrust bearing surface includes non-zero components in the radially outward direction, in the upstream direction, and in the circumferentially forward direction. As best seen in FIG. 3, vector X projects in the upstream direction U and projects radially outward, away from the axis of rotation R.

Further in this embodiment, the rotor body 310 includes a principal surface of revolution about the axis R, generally defined as the peripheral surfaces of vanes 311, that is substantially cylindrical in shape. The substantially cylindrical principal surface of revolution generally has an outside diameter, which is preferably about 4 to about 12 mm in the case of a blood pump 300 intended for intravascular implantation in an adult human, and more preferably about 9 to 11 mm. Vanes 311 define chamfer or beveled surfaces 313 at the upstream ends of the vanes 311. The chamfer surfaces 313 slope radially outwardly in the downstream direction, so that the chamfer surfaces 313 are generally in the form of portions of a conical surface of revolution about the axis having increasing diameter in the downstream direction. As illustrated in FIG. 3, the downstream diameter of the chamfer surfaces 313 may be substantially equal to the first diameter of the vanes 311 and the cylindrical surface of revolution of body 310. Thrust bearing surfaces 330 are provided as portions of the chamfer surfaces 313. Thrust bearing surfaces 330 are recessed relative to surrounding portions of the chamfer surfaces 313 such that each thrust bearing surface 330 defines a pocket in the chamfer surfaces 313. Each pocket, defining thrust bearing surface 313, includes a leading portion 338 and a trailing portion 340 in the rotation direction. The pocket has a progressively increasing depth such that the deepest portion of the pocket is at leading portion. Stated another way, each thrust bearing surface 330 slopes progressively outward, toward the surrounding chamfer surface 313, in the direction from the leading portion to the trailing portion. Moreover, the leading portion is open to adjacent channel 320. The difference between the thrust bearing surface 330 at leading portion and the chamfered surface 313, measured adjacent to leading portion, defines a radial gap height, which may be within the range of about 0.0010 inches to about 0.0020 inches, such as, for example, 0.0010 inches, 0.0015 inches, 0.0020 inches, or the like.

The chamfer surfaces 313 define a chamfer angle A such that the chamfer surfaces 313 are positioned at an angle relative to axis R and relative the generally cylindrical surface of revolution of the rotor body 310. Chamfer angle desirably is in the range of about 20 degrees to about 45 degrees, and typically is less than 45 degrees. For example, the chamfer angle A of the chamfer surfaces 313 may be about 30 degrees. The chamfer surfaces 313 have a chamfer length L measured in the axial directions which may be in the range of about 0.06 inches (1.5 mm) to about 0.1 inches (2.5 mm). In one example, the chamfer length L is about 0.08 inches (2 mm).

The rotor body 310 may further include and projection members 334 and 336 extending upstream and downstream from the vanes 311. The particular example of the rotor 300 shown in FIG. 3 includes four vanes 311 defining four channels 320, each vane 311 having two radial bearings 331 on the blade tips of the vanes 311 defining the cylindrical surface of revolution of body 310. Each radial bearing 331 is formed as a recessed pocket in the peripheral surface of the vane 311, and each such pocket has its maximum depth at the leading edge of the pocket, i.e., the edge of the pocket which lies at the circumferentially forward side. The depth of each pocket 331 decreases progressively toward the trailing end of the pocket 331. The radial bearing pockets 331 are open to channels 320 at the leading edges of the pockets 331. Any number of vanes 311 and radial bearings 331 is contemplated.

Rotor body 310 is positioned within a hollow casing 302. The hollow casing 302 defines flow path therethrough, within which the rotor body 310 is positioned. Casing 302 also includes an upstream end and a downstream end, corresponding to the direction of fluid flow F, and corresponding to the upstream and downstream ends of the rotor 310. The flow path has a central axis R coincident with the central axis of the rotor 310, an inlet 304 at its upstream end and an outlet 306 at its downstream end. Casing 302 further includes a mechanical stop surface 309 positioned upstream of vanes 311 and chamfer surfaces 313 of rotor body 310. The stop surface 309 is intended to prohibit excessive upstream motion of the rotor body 310 out of its ordinary position.

As shown in FIG. 3, the stop surface 309 is positioned adjacent to a portion of the rotor body 310 and may be shaped similarly to such portion of body 310. In this embodiment, the stop surface 309 is substantially in the form of a surface of revolution about the central axis R, such surface facing inwardly toward the central axis. The stop surface 309 has a diameter increasing progressively in the downstream direction. In this embodiment, the stop surface 309 is substantially conical, and lies at an angle A to the central axis which is substantially equal to the angle A of the chamfer surfaces 313. The stop surface 309 may have a length in the axial direction approximately equal to the length L of the chamfer surfaces 313. The smaller (minor) inside diameter of the stop surface 309 should be less than the outside diameter defined by the vanes 311. The main portion of the flow path 305, downstream from stop surface 309, desirably has an inside diameter just slightly larger than the outside diameter OD defined by the vanes 311 on the rotor 310.

The casing 302 may include additional features such as a downstream stop (not shown) to prevent movement of the rotor out of the casing through the outlet 306 while the pump 300 is inactive. Also, a set of stationary vanes, sometimes referred to as a "diffuser" (not shown) may be positioned downstream from the rotor 310. The vanes of the diffuser may be arranged to reduce rotation of fluid around the axis R.

A motor stator 324 is disposed in proximity to casing 302 and outside of the flow path and preferably surrounding at least a portion of the rotor body 310. The stator 324 may include one or more electromagnetic coils, most commonly a plurality of coils such as three coils disposed at equal 120 degree intervals about the central axis R, as discussed above and as is known in the art. In operation, a power source (not shown) creates alternating currents which pass through the coils, to create a magnetic field in a direction transverse to axis R and rotating axis R. This field is applied to the rotor so as to rotate the rotor body 310 about axis R. The magnetic field of the stator also tends to hold the rotor in position along the axis, in alignment with the stator. As discussed above, this effect is referred to as the axial magnetic stiffness of the stator.

Casing 302 may be made of any non-ferromagnetic material capable of handling the rotor 310 operation, which substantially resists thrombosis, and which is biocompatible. Desirably, the casing material should be resistant to mechanical wear. For example, the material of casing 302 may be a ceramic. Rotor body 310 includes a magnetically hard ferromagnetic material, i.e., a material which forms a strong permanent magnet and which is resistant to demagnetization. The material of the rotor body also should be biocompatible and substantially non-thrombogenic. For example, the rotor body may be formed as a unitary mass of an alloy of platinum and cobalt. In other embodiments, the rotor body may be formed from a magnetic metal such as an iron-nickel alloy with an exterior coating of another material to increase the body's biocompatibility. The rotor is magnetized with a magnetic field transverse to the axis R, so as to provide magnetic poles at the peripheral surfaces of the vanes.

In operation, the stator 324 is actuated by the power source to provide a rotating magnetic field and thus spin the rotor 310 about axis R. As the rotor 310 spins, the radial bearings 331 hold the rotor 310 centered within the flow path of the housing 302 and out of contact with the wall 302. The radial bearings 331 operate as hydrodynamic bearings. A small portion of the blood passing through the pump 300 enters the pockets of the radial bearings 331, and encounters the sloping pocket surfaces. This interaction generates forces on the rotor 310 directed radially inwardly, toward the axis.

A small portion of the blood flowing within the flow path passes between the chamfer surfaces 313 of the rotor 310 and the stop surface 309 of the casing 302. This blood enters into the pockets defined by thrust bearing surfaces 330. The thrust bearings also operate as hydrodynamic bearings. As the rotor 310 turns, the blood contained in the pockets applies forces to the thrust bearing surfaces 330. These forces are directed approximately normal to the bearing surfaces. Thus, the forces are directed along vector V, approximately opposite to the normal vector X of each thrust bearing surface. The forces on the thrust bearing surfaces 330 thus have components directed radially inwardly, toward axis R, and also have components directed in the downstream direction D.

In some embodiments, a stator magnet 332 may be positioned in the stop surface 309. The stator magnet 332 may have an attraction force between a corresponding magnet 322 or magnets 322 of the rotor 310. The attraction force between the stator magnet 332 and the rotor magnets 322 may counteract the thrust bearing force from the interaction between surface 313 and the stop surface 309 and may maintain the rotor 310 in a preferred position within the flow path. The rotor magnets 322 may be positioned in the upstream portion 334 or may reside in chamfer surface 330, or along the main body of rotor 310.

Alternatively, the stator magnet 332 may be used to provide a repelling force between a corresponding magnet 322 of the rotor 310. This may be particularly useful when operating the pump 300 at higher speeds and/or capacity. The repelling forces between stator magnet 332 may also allow the pump 300 to be operated at higher rotational speeds than a comparable pump without the repelling magnets 332, 322, to provide a greater pressure differential, greater flow rate or both. In some embodiments, the magnets 332 may be actively controlled to adjust the magnetic forces as impeller speeds change or as the gap between the bearing 309 and the rotor 310 change.

Figure 4:
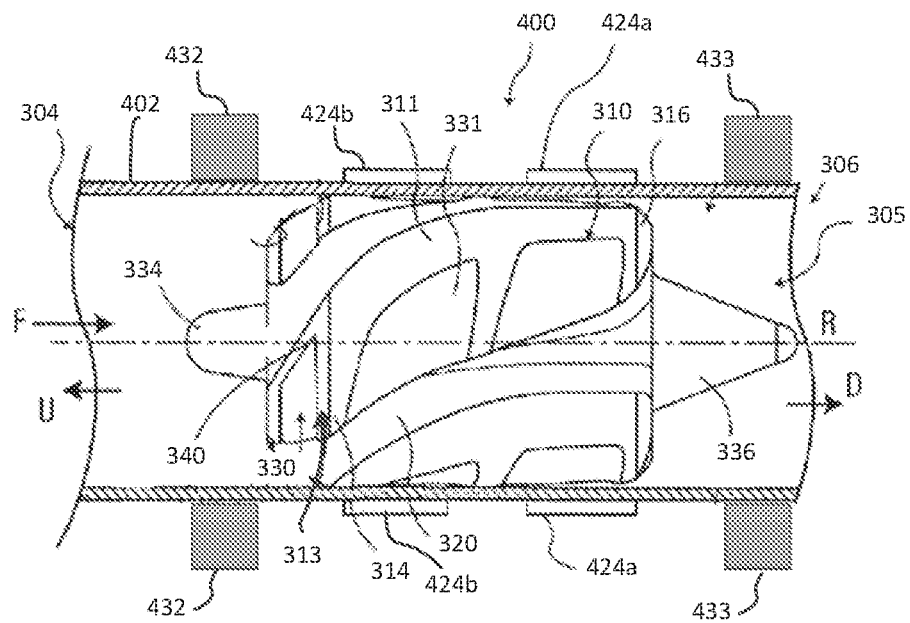
FIG. 4 illustrates another blood pump that is a modified version of the blood pump illustrated in FIG. 3 according to some embodiments of the present invention.

While the pump 200 illustrated in FIG. 2 and the pump 300 illustrated in FIG. 3 include a constriction 209, 309 respectively to provide increased axial (translation along the Z-axis) and/or tilt stabilization (rotation off of the Z-axis), it should be understood that other embodiments may avoid the use of a constriction in the upstream or downstream directions. For example, FIG. 4 illustrates exemplary pump 400. Exemplary pump 400 is a modified version of pump 300 of FIG. 3. As illustrated, pump 400 may include similar features as pump 300, however housing 402 of pump 400 may not define an upstream constriction portion 309 of the flow path to provide for axial and tilt stabilization of the rotor 310. Pump 400 may utilize permanent magnets 432 positioned upstream from an axial center of the rotor 320 to provide axial stabilization of the rotor 320 within the flow path. Additionally or alternatively, the pump 400 may utilize permanent magnets 433 positioned downstream from an axial center of the rotor 320 to provide axial stabilization of the rotor 320 in the flow path. For example, the upstream magnets 432 may provide a repulsion force against the rotor 310 as the rotor 310 is in operation to urge the motor 310 in a downstream direction and the downstream magnets 433 may provide a repulsion force against the rotor 310 to urge the motor 310 in an upstream direction. In some embodiments, if forces acting on the rotor 310 at higher operating speeds tend to urge the rotor 310 in an upstream direction, magnets 433 may provide an attractive force on the rotor 310 to urge the rotor 310 in the downstream direction and to counter the forces at the higher speeds.

Moreover, in some embodiments, as illustrated in FIG. 4, the motor stator of the pump 400 may have two separate components 424a and 424b. Motor stator 424a may be generally positioned about the downstream portion of the rotor 320 and motor stator 424b may be generally positioned about the upstream portion of the rotor 320. Both motor stators 424a, 424b may act in concert to drive rotor 320 of pump 400. Additionally, each motor stator 424a, 424b may provide additional axial stiffness to stabilize the rotor 320 in the axial direction within the flow path. Moreover, the motor stator 424a may provide additional tilt stabilization of the rotor 320 as it is positioned generally about a downstream portion of the rotor 320 while motor stator 424b may provide additional tilt stabilization of the rotor 320 as it is positioned generally about an upstream portion of the rotor 320.

Thus in some embodiments, a pump 400 may be provided without a constriction (e.g., constriction 209, 309) in the flow path. The pump may provide axial and tilt stabilization through the use of one of or a combination of: active control of a plurality of motor stators that are offset a distance from an axial center of the rotor, magnets 432 positioned upstream of the rotor 310, and/or magnets 433 positioned downstream of the rotor 310.

Figure 5:
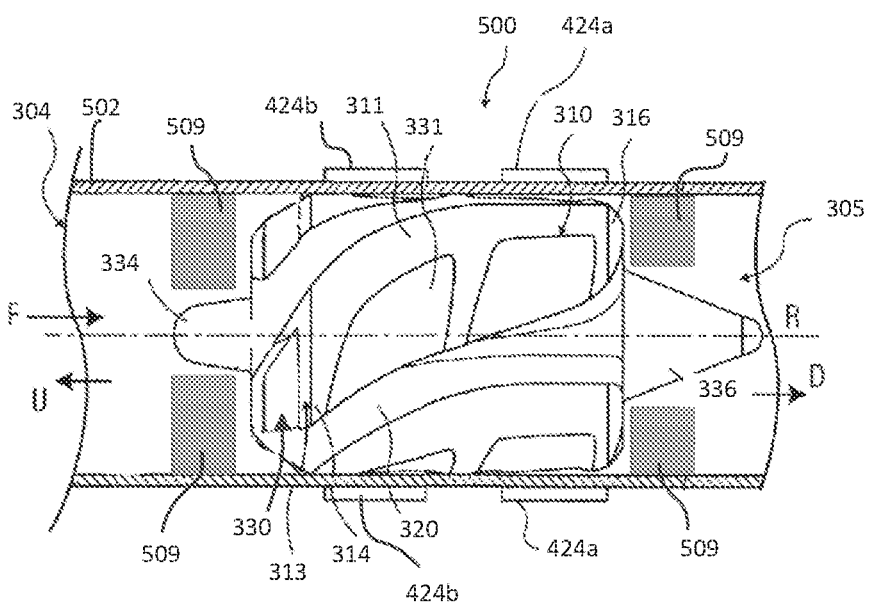
FIG. 5 illustrates yet another blood pump that is another modified version of the blood pump illustrated in FIG. 3 according to some embodiments of the present invention.

FIG. 5 illustrates another exemplary pump 500 according to some embodiments of the invention. Exemplary pump 500 is a modified version of pump 300 of FIG. 3. Pump 500 may have a housing 502 defining a flow path from the inlet 304 to the outlet 305. The flow path may include a step bearing 509 upstream from the rotor 310. The step bearing may take the place of the constriction 309 and may provide axial stabilization of the rotor 310 within the flow path. Additionally, step bearings 309 may be positioned downstream of the rotor 310 to provide axial stabilization in the downstream direction. The step bearings 509 may have hydrodynamic bearing surfaces or may provide a surface where hydrodynamic bearings of the rotor 310 interact to provide the axial stabilization forces for the rotor 310. While not illustrated, it should be appreciated that downstream end 316 of rotor 310 may include a hydrodynamic bearing surface that cooperates with the downstream step bearings 509 to provide axial stabilization. Pump 500 may also utilize a two part motor stator 424a, 424b similar to pump 400. As discussed above, the two part motor stator 424a, 424b may be positioned on opposite sides of an axial center of the rotor 310 or may otherwise drive opposite ends of the rotor 310. In addition to providing axial stabilization, the motor stators 424a, 424b may provide additional tilt stabilization for the rotor 310 so as to reduce wobbling of the rotor 310 during operation. Further at different pump speeds, the motor stators 424a, 424b may be controlled to bias the rotor 310 in the upstream or downstream direction as needed so as to maintain the rotor 310 at a desired axial position.

Figure 6:
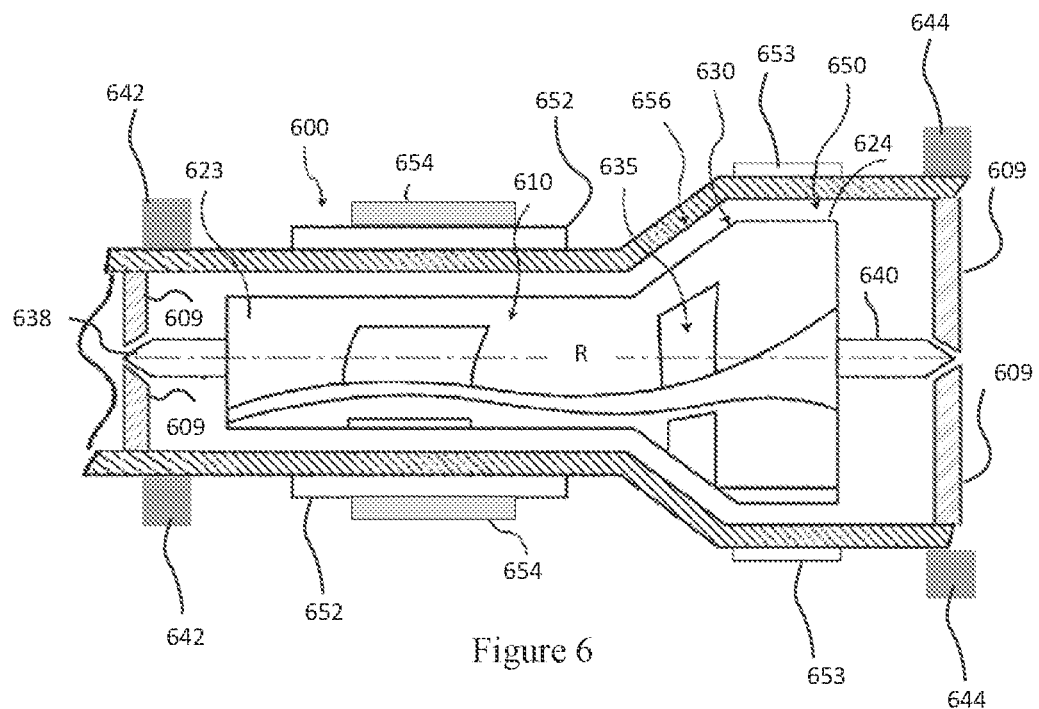
FIG. 6 illustrates yet another blood pump with stabilization components according to some embodiments of the present invention.

A pump according to a further embodiment of the invention includes a rotor body 610 (FIG. 6) positioned within a casing 650. In this embodiment, the vanes or blades of the rotor 610 flare radially outwardly and define chamfer surfaces 630 near the downstream end 624 of rotor body 610 rather than at the upstream end 623. In this embodiment, the body 610 includes a substantially cylindrical body, but has a portion having a first diameter and a portion having a second diameter. The two portions are separated by the chamfer surfaces 630. Chamfer surfaces 630 are provided with thrust bearing surfaces 635, similar to thrust bearing surfaces of the embodiments discussed above. Casing 650 includes stop surface 656, which in this example is positioned downstream of the stator 652. Here again, the stop surface 656 has a form of at least a portion of a surface of revolution about axis R. This surface has a diameter which increases progressively in the downstream direction along the bore axis R. Pump 600 operates in a similar fashion as the pumps discussed above. Here again, rotor body 620 is prevented from migrating upstream by combined action of the magnet stiffness of stator 652 and the force generated by thrust surfaces 635.

Optionally, to provide further axial stabilization, upstream and/or downstream conical bearings 609 may be provided to cooperate with the front portion 638 and/or back portion 640 of rotor 610. Conical bearings 609 may extend from the housing 650 and into the flow channel. The conical bearings 609 may form a conical opening for cooperating with the upstream and or downstream portions. The conical bearings 609 may provide additional axial and tilt stabilization of the rotor 610 during operation. Additionally, or alternatively, upstream permanent magnets 642 and/or downstream magnets 644 may be provided to bias the rotor 610 in the upstream and/or downstream directions for axial stabilization of the rotor 610. In some embodiments, it may be preferable if the upstream magnets 642 are configured to bias the rotor 610 to urge it in a downstream direction. Magnets 644 may be configured to provide either a biasing force in the upstream direction or in the downstream direction. The biasing force provided by downstream magnets 644 may depend on a thrust bearing 635 configuration and/or a pump speed. In some embodiments, the magnets 644 may be actively controlled to adjust the magnetic forces as impeller speeds change or as a gap between surface 630 and surface 656 change. Additionally, it should be appreciated that the attractive/repulsive forces by magnets 642 and 644 may be adjusted by adjusting a distance between the magnets 642, 644 and the rotor 610.

In some embodiments it may be preferable to provide a higher attractive force on the upstream end and a less attractive force or a repulsive force on the downstream end, such a configuration may provide additional tilt stabilization. As discussed above, the higher attractive force on the upstream end may be controlled actively, may be provided by a larger magnet, and/or may be provided by a shorter distance between the upstream magnet 642 and the rotor 610 relative to a distance between the downstream magnet 644 and the rotor 610.

Additionally, or alternatively, a second motor stator 653 may be provided about the downstream portion 624 of the rotor 610. The second motor stator 653 may also be driven to rotate the rotor 610 in the blood flow path. Further, the second motor stator 653 may provide additional tilt stabilization of the downstream portion 624 while the motor stator 652 may provide tilt stabilization of the upstream portion 623.

In some embodiments, a yoke 654 may contact the stators 652 and increase the EMF output to provide additional axial stiffness. For example, in some embodiments, the yoke 654 may be a ring of iron or Permalloy™ material above and/or below the stators 652. While illustrated with a yoke 654 on stator 652, it may be beneficial to provide yoke 654 on magnets 642, stator 653, and/or magnet 644 to increase a magnetic flux density associated with the magnet. It should also be appreciated the yokes 654 may be utilized in combination with other magnets of the above embodiments to increase a magnetic flux density of the magnets as needed to provide additional axial and/or tilt stabilization.

Figure 7:
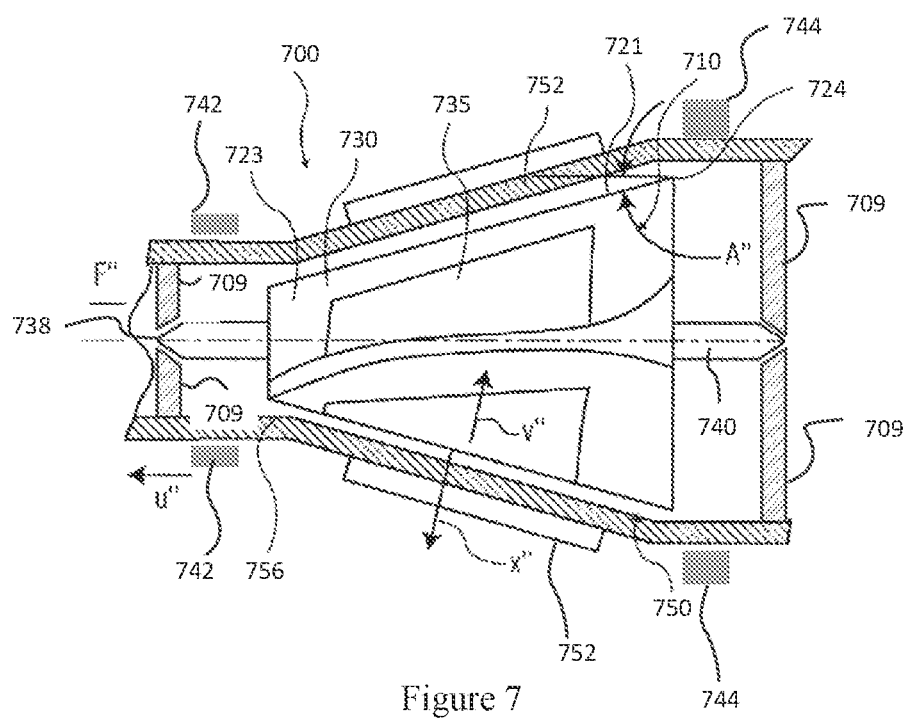
FIG. 7 illustrates yet another blood pump with stabilization components according to some embodiments of the present invention.

FIG. 7 illustrates yet another embodiment of a blood circulating pump 700. In this embodiment, the vanes or blades of the rotor 710 progressively increase in diameter along the length of the body. Thus, the main portion of rotor body 710 has a tapered peripheral surface 721 generally in the form of a surface of revolution about axis R having progressively increasing diameter in the downstream direction. In the particular embodiment depicted, the peripheral surface 721 of the rotor main portion is a cone having a generatrix disposed at an angle A to axis R. This peripheral surface is provided with bearing surfaces 735. The casing 750 includes a bore with an interior surface 756 which also has a diameter which increases progressively in the downstream direction along the axis R. The inwardly facing surface 756 is complementary to the outwardly facing peripheral surface 721 of the rotor 710. Thus, surface 756 may be a conical surface having a generatrix disposed at approximately the same angle A to axis R. Also in this example, the stator 752 surrounds at least a portion of the interior surface 756 and tapered peripheral surface 721 of the rotor. In this embodiment, each bearing surface 735 has a normal vector X with a positive, non-zero component in the upstream direction U and also in the radially outward direction, away from axis R. The normal vector X desirably also has a component in the circumferentially forward direction. Upon rotation of rotor 710 about axis R in the forward direction, each bearing surface 735 will be subjected to forces directed along vector V, with both downstream and radially inward components. Thus, bearing surfaces 735 act as radial bearings to keep the rotor 710 centered in the bore of the housing 750, and also act as thrust bearing surfaces to provide downstream forces on the rotor. The angle A may be relatively small as, for example, a few degrees while still providing sufficient downstream force component.

To provide additional axial stabilization, conical bearings 709 may be provided upstream and/or downstream of rotor 710. The conical bearings 709 may extend into the blood flow path from the housing 750 and may cooperate with the front end 738 and/or the back end 740 to provide increased axial stabilization of the rotor 710 in the blood flow path.

Additionally, or alternatively, similar to the embodiments described above, stator magnets 742 and/or magnets 744 may be provided upstream and/or downstream from the rotor 710 and may be configured to bias or urge the rotor 710 toward a preferred axial position. The magnets 742, 744 may be configured to counter axial forces in the upstream and/or downstream direction so as to maintain the rotor 710 in a preferred position. For example, in some embodiments, the magnets 744 may be configured to urge the rotor 710 upstream toward the surface 756. In some embodiments, when the rotor 710 is at rest, the rotor 710 will rest against surface 756. However, during operation, due to hydrodynamic forces of bearings 735, the rotor 710 may be preferably spaced apart from wall 756. In some embodiments, the magnets 742 may also be configured to urge the rotor 710 in the upstream direction toward surface 756. This may be beneficial for preimplantation of the pump 700 such that the rotor 710 does not shift within housing 750 during implantation. In some embodiments, when rotor 710 experiences increased forces in the upstream direction, magnets 742 and/or magnets 744 may be configured to counter the upstream forces so that the rotor 710 maintains a preferred position within housing 750. In some embodiments, the magnets 742,744 may be configured to provide opposing forces relative to one another. For example, magnets 742 may be configured to urge the rotor 710 in the downstream direction while magnets 744 may be configured to urge the rotor 710 in the upstream direction. As discussed above, one or more yokes may be applied to the magnets and or motor stator of pump 700 to increase a magnetic flux associated with the magnet and/or motor stator.

Optionally, similar to embodiments described above, in addition or in the alternative to motor stator 752 may be configured to rotate the rotor 710 and to bias the rotor 710 in a direction toward the bearing surface 756.

Figure 8:
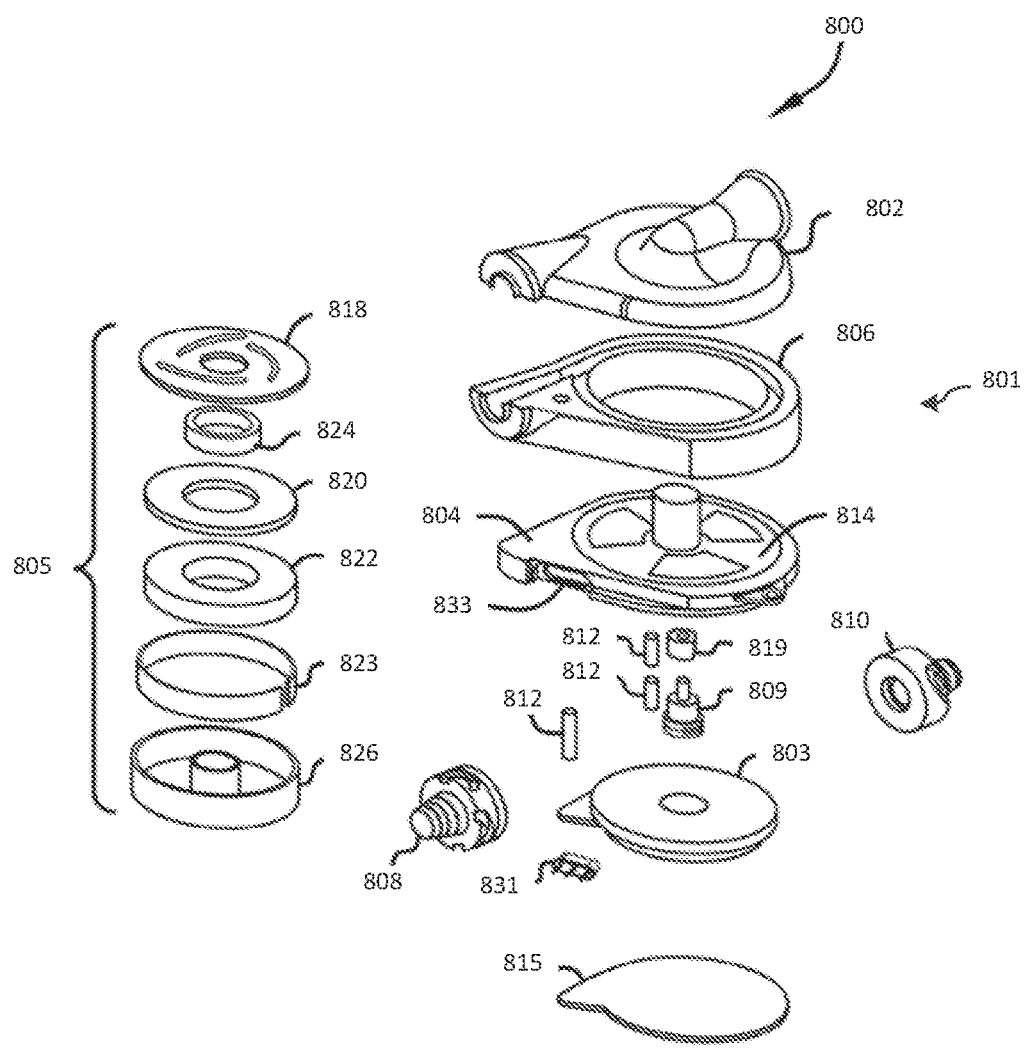
FIG. 8 illustrates an exemplary centrifugal pump according to some embodiments of the present invention.

In alternative embodiments, the stabilization device described above may be used in centrifugal pumps. In the centrifugal pumps, the rotors are shaped to accelerate the blood circumferentially and thereby cause it to move toward the outer rim of the pump, whereas in the axial flow pumps the rotors are more or less cylindrical with blades that are helical, causing the blood to be accelerated in the direction of the rotor's axis. FIG. 8 illustrates an exemplary centrifugal pump 800 according to some embodiments. This exploded view illustrates three main assemblies that makeup the rotary blood pump 800: the pump housing assembly 801, a motor assembly 803 and the rotor assembly 805.

Generally speaking, the pump housing assembly 801 makes up the main body of the rotary blood pump 800, including a housing top 802 and a housing bottom 804 which fastens by welding and aligned by alignment pins 812 to a top and bottom side of a housing middle 806

As seen in FIG. 8, the rotor assembly 805 is not physically connected to the housing assembly 801. Instead, the rotor assembly 805 is supported by an axial hydrodynamic bearing created between a thrust plate 814 and a bottom surface of the rotor assembly 805, a radial hydrodynamic bearing between the inside diameter of the rotor assembly 805 and the outside diameter of the spindle portion of the thrust plate 814 (additionally, or in the alternative, between the outside of the rotor assembly 805 and the inside diameter of the housing assembly 801), and by an axial magnetic bearing created between a spindle magnet 819 and a rotor axial magnet 824. The nature of these bearings is discussed in detail in U.S. Pat. No. 7,431,688, entitled Rotary Blood Pump, which is incorporated herein by reference. In some embodiments, one or more of the stabilization devices discussed above may be utilized with the centrifugal pump 800 to provide additional axial, radial, and tilt stabilization. For example, cooperating chamfer surfaces may be provided between the outer surface of spindle portion of the thrust plate and the inside diameter of the rotor assembly. Additionally or alternatively, a cooperating chamfer surfaces may be provided between the outside surface of the rotor assembly 805 and the inner surface of housing assembly 801 (e.g., inside surface of middle portion 806). Alternatively, one or more permanent magnets may be provided to urge the rotor 805 in the upstream direction (or alternatively in the downstream direction). Thus, during operation, contact between the rotor assembly 805 and the housing assembly 801 are minimized and, in one embodiment, even reduced to zero contact, thereby reducing friction, minimizing heat generation, and decreasing power requirements over prior art designs.

U.S. Pat. Nos. 5,695,471, 8,672,611, and 9,512,852 illustrate alternative centrifugal pumps which may benefit from stabilization features described herein, each of the disclosures of which are incorporated herein by reference.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A blood pump comprising:
  a housing comprising an inner wall surface defining an inlet, an outlet downstream from the inlet, and a blood flow channel between the inlet and the outlet, wherein a first portion of the inner wall surface has a first inner dimension that increases to a second inner dimension in a downstream direction;
  an axial flow impeller positioned within the blood flow channel downstream of the first portion of the inner wall surface and rotatable within the blood flow channel to pump an axial blood flow along the blood flow channel, the axial flow impeller comprising a magnetic material and at least one hydrodynamic thrust bearing surface having an outer dimension that is greater than the first inner dimension of the inner wall surface such that blood flowing between the first portion of the inner wall surface and the at least one hydrodynamic thrust bearing surface applies a pressure to the at least one hydrodynamic thrust bearing surface and prevents the axial flow impeller from advancing upstream of the first portion of the inner wall surface;
  a motor stator positioned about the blood flow channel between the inlet and the outlet, wherein the motor stator is configured to generate a magnetic field for suspending and rotating the axial flow impeller within the blood flow channel; and
  wherein the magnetic field generated by the motor stator is configured to bias the axial flow impeller such that the magnetic field urges the axial flow impeller in an upstream direction toward the first portion of the inner wall surface to stabilize the axial flow impeller in an axial direction.

2. The blood pump of claim 1, wherein the magnetic field of the motor stator urging the axial flow impeller in the upstream direction and hydrodynamic forces between the axial flow impeller and the first portion of the inner wall surface are configured to provide increased stabilization of the axial flow impeller in the axial direction.

3. The blood pump of claim 1, wherein the blood pump does not include permanent magnets.

4. The blood pump of claim 1, further comprising:
  a first permanent magnet producing a first permanent magnetic field urging the axial flow impeller in the downstream direction; and
  a second permanent magnet producing a second permanent magnetic field urging the axial flow impeller in the upstream direction;
  wherein the first permanent magnetic field and the second permanent magnetic field are configured to provide increased stabilization of the axial flow impeller in the axial direction.

5. The blood pump of claim 4, wherein:
  the first permanent comprises a first permanent magnet positioned about the blood flow channel; and
  the second permanent magnet comprises a second permanent magnet positioned about the blood flow channel.

6. The blood pump of claim 4, further comprising a first conical bearing extending into the blood flow channel, wherein:

the axial flow impeller cooperates with the first conical bearing to provide increased stabilization of the axial flow impeller in a tilt direction; and the first permanent magnetic field and the second permanent magnetic field cumulatively urge the axial flow impeller towards the first conical bearing.

7. The blood pump of claim 4, further comprising a yoke disposed about the motor stator, the yoke configured to increase a magnetic flux density associated with the motor stator.

8. The blood pump of claim 4, further comprising a yoke disposed about the first permanent magnet, the yoke configured to increase a magnetic flux density associated with the first permanent magnet.

9. The blood pump of claim 4, further comprising a yoke disposed about the second permanent magnet, the yoke configured to increase a magnetic flux density associated with the second permanent magnet.

10. The blood pump of claim 4, wherein the first permanent magnetic field and the second permanent magnetic field cumulatively urge the axial flow impeller in an upstream direction towards the first portion of the inner wall surface.

11. The blood pump of claim 4, further comprising a first conical bearing extending into the blood flow channel, wherein the axial flow impeller cooperates with the first conical bearing to provide increased stabilization of the axial flow impeller in a tilt direction.

12. The blood pump of claim 11, wherein the axial flow impeller has a hub with a conical upstream portion configured to cooperate with the first conical bearing to provide increased stabilization of the axial flow impeller in the tilt direction.

13. The blood pump of claim 11, wherein the axial flow impeller has a hub with a conical downstream portion configured to cooperate with the first conical bearing to provide increased stabilization of the axial flow impeller in the tilt direction.

14. The blood pump of claim 11, wherein the axial flow impeller comprises blades extending radially from a hub, the blades comprising beveled downstream edges configured to cooperate with the first conical bearing to provide increased stabilization of the axial flow impeller in the tilt direction.

15. A method of operating a blood pump comprising a housing an axial flow impeller, and a motor stator, wherein the housing comprises an inner wall surface defining an inlet, an outlet downstream from the inlet, and a blood flow channel between the inlet and the outlet, wherein a first portion of the inner wall surface has a first inner dimension that increases to a second inner dimension in a downstream direction, wherein the axial flow impeller is positioned within the blood flow channel downstream of the first portion of the inner wall surface and rotatable within the blood flow channel to pump an axial blood flow along the blood flow channel, the axial flow impeller comprising a magnetic material and at least one hydrodynamic thrust bearing surface having an outer dimension that is greater than the first inner dimension of the inner wall surface such that blood flowing between the first portion of the inner wall surface and the at least one hydrodynamic thrust bearing surface applies a pressure to the at least one hydrodynamic thrust bearing surface and prevents the axial flow impeller from advancing upstream of the first portion of the inner wall surface, the method comprising:

operating a motor stator positioned about the blood flow channel between the inlet and the outlet to generate a magnetic field for suspending and rotating the axial flow impeller within the blood flow channel, wherein the magnetic field urges the axial flow impeller in an upstream direction toward the first portion of the inner wall surface stabilize the axial flow impeller in an axial direction.

16. The method of claim 15, wherein the magnetic field of the motor stator urging the axial flow impeller in the upstream direction and axial hydrodynamic forces between the axial flow impeller and the first portion of the inner wall surface are configured to provide increased stabilization of the axial flow impeller in the axial direction.

17. The method of claim 15, wherein the blood pump does not include permanent magnets.

18. The method of claim 15, wherein:

the blood pump further comprises a first permanent magnet producing a first permanent magnetic field urging the axial flow impeller in the downstream direction and a second permanent magnet producing a second permanent magnetic field urging the axial flow impeller in the upstream direction; and the first permanent magnetic field and the second permanent magnetic field are configured to provide increased stabilization of the axial flow impeller in the axial direction.

19. The method of claim 15, wherein the blood pump further comprises a yoke disposed about the motor stator, the yoke configured to increase a magnetic flux density associated with the motor stator.

20. The method of claim 15, wherein:

the blood pump further comprises a first conical bearing extending into the blood flow channel; and the axial flow impeller cooperates with the first conical bearing to provide increased stabilization of the axial flow impeller in a tilt direction.

* * * * *